(12) United States Patent
Kimour et al.

(10) Patent No.: US 9,234,827 B2
(45) Date of Patent: Jan. 12, 2016

(54) METHOD AND APPARATUS FOR DETERMINING RELATIVE CONTENT OF TWO ROCK SPECIE IN A WELLBORE ROCK SAMPLE

(71) Applicant: Geoservices Equipements, Roissy en France (FR)

(72) Inventors: Farouk Kimour, Courbevoie (FR); Eric Villard, Ver-sur-Launette (FR); Pawel Kasprzykowski, Paris (FR)

(73) Assignee: GEOSERVICES EQUIPEMENTS, Paris Nord II (FR)

( * ) Notice: Subject to any disclaimer, the term of this patent is extended or adjusted under 35 U.S.C. 154(b) by 54 days.

(21) Appl. No.: 14/362,599

(22) PCT Filed: Dec. 14, 2012

(86) PCT No.: PCT/IB2012/057352
§ 371 (c)(1),
(2) Date: Jun. 3, 2014

(87) PCT Pub. No.: WO2013/088415
PCT Pub. Date: Jun. 20, 2013

(65) Prior Publication Data
US 2015/0087071 A1   Mar. 26, 2015

(30) Foreign Application Priority Data
Dec. 14, 2011 (EP) .................................... 11306660

(51) Int. Cl.
*G01N 33/24* (2006.01)
*G01N 7/18* (2006.01)

(52) U.S. Cl.
CPC . *G01N 7/18* (2013.01); *G01N 33/24* (2013.01)

(58) Field of Classification Search
CPC ................................. G01N 33/24; G01N 7/18
USPC ........ 166/250.01, 250.15–250.16; 422/82.13, 422/83; 436/25, 29, 31–33
See application file for complete search history.

(56) References Cited

U.S. PATENT DOCUMENTS 1,229,803 A * 6/1917 Spahr ................. G01N 21/8483
422/82.05
3,801,281 A * 4/1974 Thompson ........... G01N 33/241
436/133

FOREIGN PATENT DOCUMENTS

| FR | 2920226 A1 | 2/2009 |
| SU | 1490601 A1 | 6/1989 |
| SU | 1718035 A1 | 3/1992 |

OTHER PUBLICATIONS

Muller, G. et al, Neues Jahrbuch für Mineralogie-Monatshefte 1971, 466-469.*
Roberts, K. et al, Minerals and the Environment 1984, 6, 72-76.*

* cited by examiner

*Primary Examiner* — Arlen Soderquist

(57) ABSTRACT

Method and apparatus for determining the relative content of a first rock species and of a second rock species in a rock sample extracted from a wellbore. The method comprises adding a reactant to the rock sample, measuring a first information ($P_{T1}$) relative to a first amount of compound produced at a first instant (T1) and a second information ($P_{T2}$) relative to a second amount of compound produced at a second instant (T2). The method also comprises calculating the relative content of the first species in the rock sample from the first information (PT1) and calculating the relative content of the second species in the rock sample from the second information $P_{T2}$). The method comprises determining a corrected amount (Cv) of compound generated by the reaction of the second species with the reactant at the first instant (T1), and calculating the relative content of the first species in the rock sample and the relative content of the second species in the rock sample based on the corrected amount (Cv).

11 Claims, 4 Drawing Sheets

METHOD AND APPARATUS FOR DETERMINING RELATIVE CONTENT OF TWO ROCK SPECIE IN A WELLBORE ROCK SAMPLE

The present invention relates to a method for determining the relative content of a first rock species and of a second rock species in a rock sample extracted from a wellbore, the method comprising the following steps:

adding a reactant to the rock sample, the reactant reacting simultaneously with the first rock species and with the second rock species to produce a compound, the rate of reaction of the reactant with the first rock species being faster than the rate of reaction of the reactant with the second rock species;

measuring a first information relative to a first cumulative amount of compound produced at a first instant and a second information relative to a second cumulative amount of compound produced at a second instant subsequent to the first instant;

calculating the relative content of the first species in the rock sample at least from the first information determined at the first instant;

calculating the relative content of the second species in the rock sample at least from the second information determined at the second instant.

When drilling an oil well or a well for another effluent (in particular gas, vapor, water), it is known to periodically recover solid samples contained in the drilling muds emerging from the well, in view of their analysis.

The recovered solid samples are analyzed to determine geological information on the nature of the formations which are drilled. Geological information can help in the determination of the presence and value of potential deposits of fluids contained in the formation.

Some analysis are performed visually, in particular to determine the cuttings lithology and to correlate it with other informations, such as depth or gaseous content. The correct construction of the lithology of the formation helps in defining the efficiency of the drilling operation. It also provides safety for further production and it helps determining the location of potential wells by delimiting appropriate geological underground structures.

Among the different analysis which are performed on site, the relative content of the different rock species which are available in the rock samples extracted from the well bore is usually determined.

In particular, the relative content of calcite and dolomite is often evaluated through geochemical methods.

To this end, a known method disclosed e.g. in FR 2 920 226 comprises adding chlorhydric acid to a calibrated sample of rock, and measuring the gaseous compound (in this case carbon dioxide) produced by the reaction of the acid with the calcite and the dolomite.

Since the calcite reacts much faster than the dolomite, the known method comprises measuring the amount of gas compound produced at a first instant, shortly after the initial addition of acid into the rock sample, to determine the calcite content. Then, the total gas compound produced at a subsequent second instant, more than a few minutes after the first measurement, is determined. The relative content of the dolomite is obtained by subtracting the content of gas compound measured at the first instant from the amount of gas compound content measured at the second instant.

This method is easy to operate, and simple to implement on a drilling site, even in remote environments.

However, when correlated to more precise methods, which can be performed in a laboratory (e.g. x-ray diffraction), it appears that geochemical method may suffer from large errors, especially when the relative content in calcite is very low.

One aim of the invention is therefore to provide a method for determining the relative contents of two rock species in the same rock sample, which can be easily implemented in the vicinity of a drilling well and which remains very accurate.

To this end, the invention concerns a method of the aforementioned type, characterized in that the method comprises:

determining a corrected amount of compound generated by the reaction of the second species with the reactant at the first instant, and calculating the relative content of the first species in the rock sample and the relative content of the second species in the rock sample based on the corrected amount.

The method according to the invention may comprise one or more of the following feature(s), taken in isolation or in any technical possible combination(s):

the determination step comprises calculating the corrected amount of compound based on at least an estimated proportionality constant estimating the relative amount of gas compound generated by the reaction of the second species with the reactant at the first instant to the total amount of compound generated by the reaction of the second species with the reactant;

the corrected amount is calculated based on at least one of the first information representative of the first amount of compound produced at the first instant and of the second information relative to the second amount of compound produced at the second instant;

the corrected amount is given by the equation $$\frac{K}{1-K}(P_{T2} - P_{T1}),$$

where K is the estimated proportionality constant, $P_{T1}$ is the first information relative to the first amount of compound produced at the first instant and $P_{T2}$ is the second information relative to the second amount of compound produced at the second instant;

the relative content of the first species in the rock sample is calculated by subtracting the corrected amount to the first information representative of the first amount of compound produced at the first instant and in that the relative amount of the second compound is calculated by adding the corrected amount to the second information representative of the second amount of compound produced at the second instant minus the first information representative of the first amount of compound produced at the first instant;

the determination step of the corrected amount comprises the following steps:

obtaining a cumulative curve relating the cumulative amount of generated compound as a function of time based at least on the first information and on the second information;

deconvoluting the cumulative curve into a first deconvoluted curve representative of the amount of compound produced by the first species as a function of time and a second deconvoluted curve representative of the amount of compound produced by the second species versus time;

calculating the relative content of the first species and the relative content of the second species based on the first deconvoluted curve and on the second deconvoluted curve;

the first deconvoluted curve comprises an exponential function, in particular a function of the type $$P_1\left[1 - \exp\left(\frac{-t}{\tau_1}\right)\right],$$

in which $P_1$ is the relative content of the first species in the rock sample, t is the time and $T_1$ is a constant representative of the kinetics of reaction of the first compound with the reactant and in that the second deconvoluted curve comprises an exponential function, in particular of the type $$P_2\left[1 - \exp\left(\frac{-t}{\tau_2}\right)\right],$$

in which $P_2$ is the relative content of the second species and $T_2$ is a constant representative of the kinetics of reaction of the second species with the reactant;

it comprises the steps of:
 measuring a curve of an information representative of the cumulative amount of compound generated as a function of time;
determining an inflexion point on the curve;
determining the first instant based on the time at which the inflexion point is calculated;
it comprises:
 measuring a curve of an information representative of the cumulative amount of compound generated as a function of time;
 fitting the curve to a pre-determined function;
 calculating an information representative of total amount of compound generated by the reaction of the reactant with the first species and with the second species based on the fitted function;
calculating the relative content of the second species in the rock sample based on the information representative of the total amount;
the first rock species is calcite and the second rock species is dolomite.

The invention also relates to a device for determining the relative content of a first rock species and of a second rock species in a rock sample extracted from a wellbore, the device comprising:
 an enclosure able to receive the rock sample and a reactant, the reactant reacting simultaneously with the first rock species and with the second rock species to produce a compound, the rate of reaction of the reactant with the first rock species being faster that the rate of reaction of the reactant with the second rock species;
a means for measuring a first information relative to a first cumulative amount of compound produced at a first instant and for measuring a second information relative to a second amount of compound produced at a second instant subsequent to the first instant;
a means for calculating the relative content of the first species in the rock sample at least from the first information determined at the first instant;
a means for calculating the relative content of the second species in the rock sample at least from the second information determined at the second instant;
characterized in that the device comprises:
 a means for determining a corrected amount of compound generated by the reaction of the second species with the reactant at the first instant; and
 a means for calculating the relative content of the first species in the rock sample and the relative content of the second species in the rock sample based on the corrected amount.

The invention will be better understood upon reading the following description, which is given solely by way of example, and which is written in reference to the appended drawings, in which.

Figure 1:
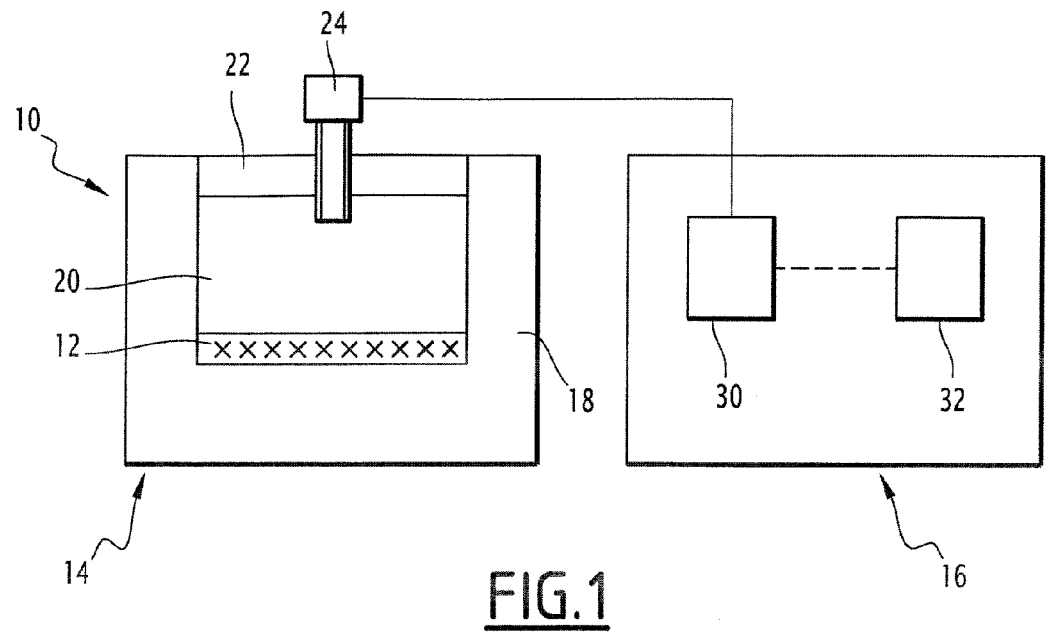
FIG. 1 is a schematic view, taken partially in cross-section, of a first device according to the invention, before starting a determining method according to the invention.

A first device 10 for determining the content of a first rock species and of a second rock species in a rock sample 12 extracted from a wellbore is shown in FIG. 1.

The rock sample 12 is for example obtained from cuttings extracted out of a drilling mud, from which the liquid has been removed. The drilling mud is continuously recovered at the outlet of the well being bored. The cuttings are for example taken in a drilling mud extraction pipe or container, in particular in a shale shaker.

The device 10 is in particular suitable for determining the relative content of a first rock species and of a second rock species available in the rock sample. The first rock species is for example calcite, having the chemical formula $CaCO_3$, and the second rock species is for example dolomite, having the chemical formula $CaMg(CO_3)_2$.

Figure 2:
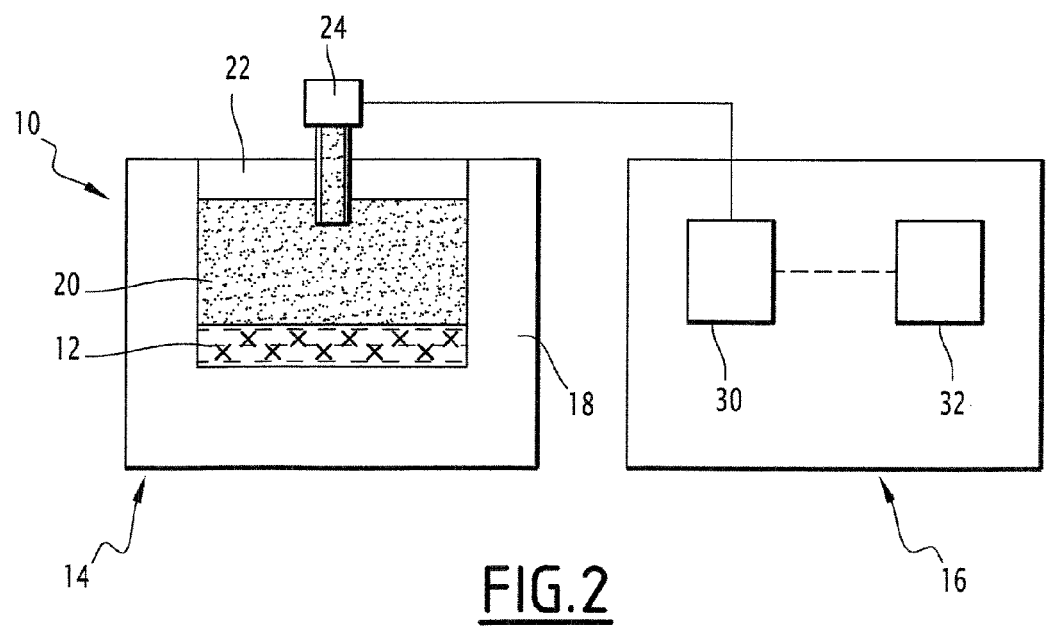
FIG. 2 is a view similar to FIG. 1, during a the operation of a determining method according to the invention.

As illustrated in FIGS. 1 and 2, the device 10 comprises a measurement cell 14 and a data acquisition and calculation unit 16.

The measurement cell 14 comprises an enclosure 18 defining an internal volume 20 which opens out of the enclosure 18.

It also comprises a closing member 22 for releasably sealing the internal volume 20 and a compound measurement sensor 24.

The enclosure 18 is able to receive the rock sample 12 and a reactant which can react simultaneously with the first rock species and with the second rock species to produce a compound.

Advantageously, the reaction of the reactant with the first species and with the second species produces a gas compound, advantageously the same gas compound.

The reactant is for example an acid, such as chlorhydric acid. The acid is able to react in the internal volume 20 with the first species and the second species to produce the compound.

In particular, the generated gas compound is carbon dioxide obtained through the following chemical reactions:

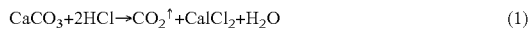
(1)

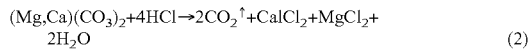
(2)

The closing member 22 is able to be moved between an insertion position, in which it allows the introduction of the rock sample 12 into the internal volume 20 and a sealing position (shown in FIG. 2) in which it seals the internal volume 20 and it maintains the gas produced by the reaction of the first and second species in the internal volume 20.

In this example, the compound measurement sensor 24 is a pressure sensor. It is able to continuously measure the pressure in the internal volume 20 as a function of time with a sampling interval of e.g 50 Hz.

The sensor 24 is connected to the data acquisition and calculation unit 16.

The data acquisition calculation unit 16 comprises a data acquisition module 30 able to record and process the information relative to the cumulative amount of compound produced at any instant, as measured by the sensor 24.

The calculator 32 is able to calculate the relative content of the first species in the rock sample 12 and the relative content of the second species in the rock sample 12 based on the information recorded by the data acquisition module 30, and to determine a corrected amount of compound generated by the reaction of the first species and the second species, at a first instant, as will be described below.

Figure 4:
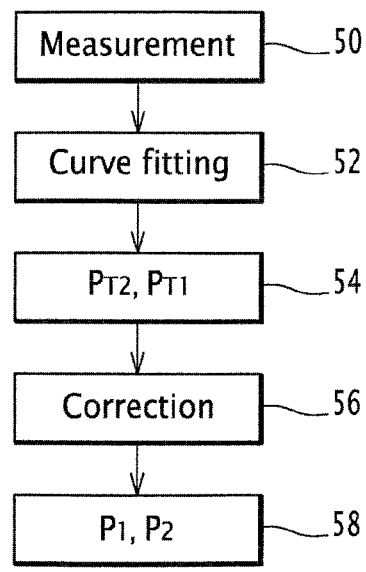
FIG. 4 is a synoptic diagram of the different steps of the first method according to the invention.

A first determining method according to the invention is illustrated in FIG. 4.

As depicted on this Figure, the measurement method comprises a measurement step 50, an optional curve fitting step 52, an information determining step 54, a correction step 56 and a relative content calculation step 58.

In the measurement step 50, a rock sample 12 is periodically obtained from the mud flowing out of a well and is prepared to be introduced in the measurement cell 14.

To this effect, the rock sample extracted from the well is separated from the liquid it contains. The rock sample is dried, e.g. in an oven.

The sampling period depends on the amount of information needed. Usually, a representative rock sample 12 is collected approximately at time intervals comprised between 5 minutes and 60 minutes.

Once dried, the sample 12 is crushed and is optionally screened to obtain a controlled granulometry.

In particular, the dried sample 12 is crushed with mechanical means such as a mortar and a pestle to form a powder. Then, the crushed powder is passed on a first sieve of minimal mesh and on a second sieve of maximal mesh to obtain a sample having a granulometry comprised between the size of the minimal mesh and the size of the maximal mesh.

In a particular example, the granulometry of the powder is chosen between approximately 0.063 mm and 0.125 mm.

A pre-determined mass of the sample 12 is then weighed and transferred into the internal volume 20 of the enclosure. The mass of the sample 12 is for example lower than 10, e.g. about one gram. The closing member 22 is then closed to seal the internal volume 20.

A pre-determined volume of reactant is subsequently introduced in the enclosure 18, in order to react with the rock sample 12.

The sample is mixed with the reactant by agitation, for example manual agitation. In a variation, a magnetic bar is used to provide agitation.

In particular, the reactant is an acid solution, e.g. a solution of chlorhydric acid. The amount of acid introduced is for example lower than 50 ml, for example approximately equal to 20 ml.

The reactant reacts simultaneously with the first rock species and the second rock species to form a gas compound.

The sensor 24 is activated to measure an information representative of the cumulative amount of gas compound generated by the reaction of the first species and of the second species contained in the rock sample 12 with the reactant.

As shown in FIG. 2, the representative information is the pressure which builds up in the internal volume. The pressure measured by the sensor 24 into the internal volume 20 gradually increases.

The pressure is measured versus time at a regular period which is for example lower than 1 second and in the order of 1 millisecond.

The pressure is representative of the cumulative amount of gas compound. In particular, the cumulative molar amount C of compound can be calculated from pressure P according to the perfect gas law:

$$C = \frac{P \cdot V}{R \cdot T}, \quad (3)$$

where V is the volume of the enclosure 18, R is the perfect gas constant, T is a temperature in the internal volume 20.

Figure 3:
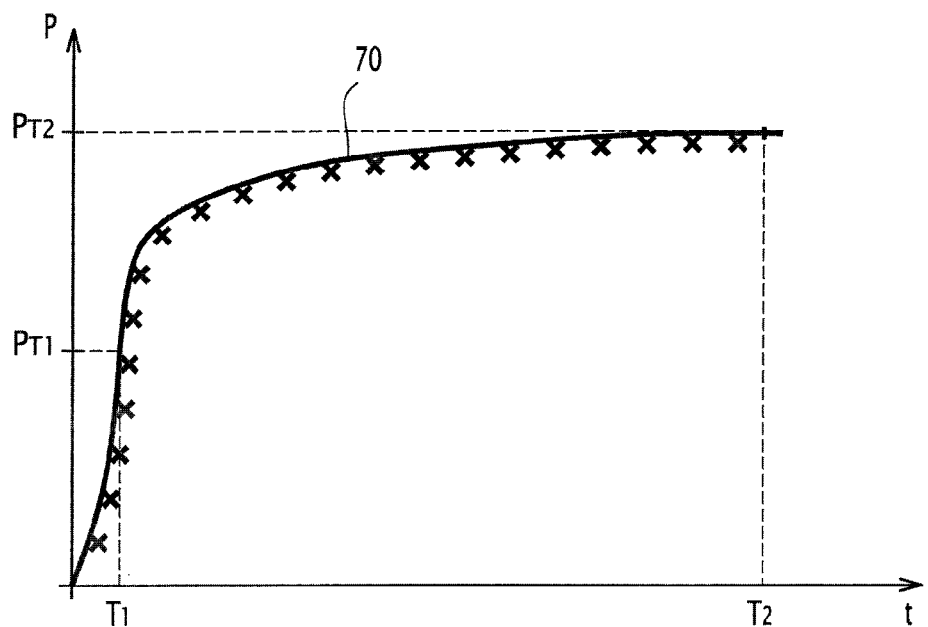
FIG. 3 is a pressure versus time curve obtained in the device of FIG. 2.

As illustrated in FIG. 3, at least a first information $P_{T1}$ relative to a first cumulative amount of compound produced is collected at a first instant T1. At least a second information $P_{T2}$ relative to a second cumulative amount of compound produced at a second instant T2 subsequent to the first instant T1 is collected.

In the particular embodiment, an information P relative to the cumulative amount C of compound produced at any instant T is collected.

In the optional curve fitting step 52, the curve 70 of the information P representative of the cumulative amount of compound as a function of time is fitted to a first predetermined function, in particular, to an exponential function.

In a particular example, the curve 70 is fit to an exponential function of the type:

$$P = A \cdot \exp\left[\frac{-t}{\tau}\right] + P_{\infty}, \quad (4)$$

where A and τ are fitting constants, t is the time and $P_{\infty}$ is a value representative of the total compound generated after an infinite time.

The curve fitting is performed by mathematical optimization methods which are known from the skilled person. In particular, the methods can be based on a least square calculation.

At step 54, a first information $P_{T1}$ representative of the gas compound generated after a short time is collected at a first instant T1, at which it is assumed that the first species has totally reacted with the reactant.

In a particular example, the first instant T1 occurs less than one minute after the start of the reaction, in particular less than 30 seconds after the start of the reaction, and in particular approximately 15 seconds after the start of the reaction.

A second information $P_{T2}$ representative of the total gas compound generated by the reaction of the first species and of the second species is also collected at a second instant T2 subsequent to the first instant T1.

Figure 5:
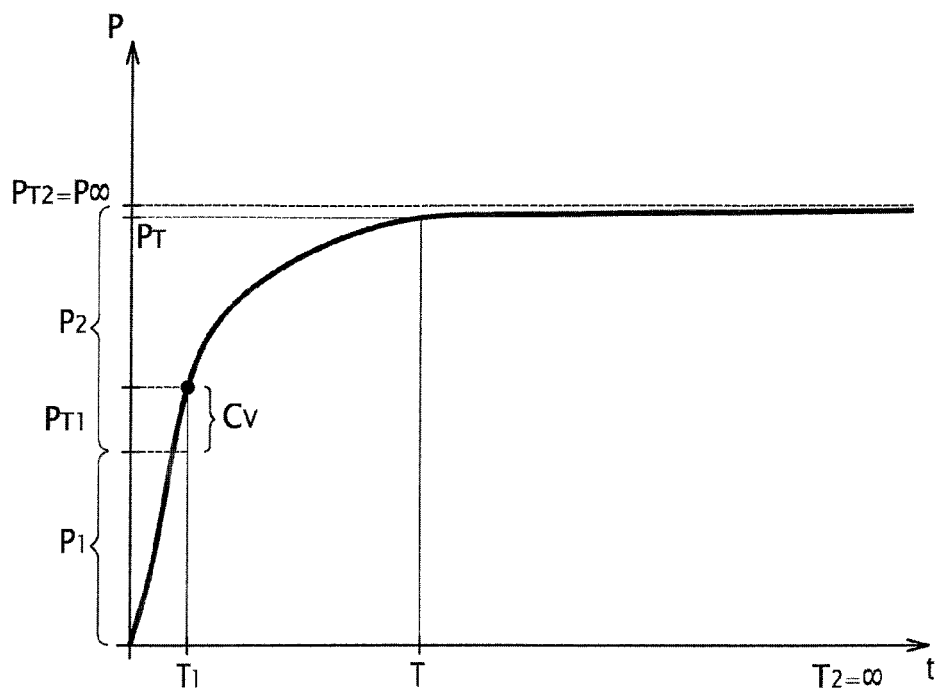
FIG. 5 is a curve of the cumulative gas compound content versus time illustrating the first method according to the invention.

In the example of FIG. 5, in which a curve fitting step 52 is performed, the second information $P_{T2}$ is calculated based on the value $P_\infty$ representative of the total amount of compound calculated from the curve fitting after an infinite time, and advantageously is equal to the value $P_\infty$.

According to the invention, in the correction step 56, a corrected amount $C_v$ of compound generated by the reaction of the second species with the reactant from the start of the reaction to the first instant T1 is calculated.

In the first method, the corrected amount $C_v$ is calculated based on a chosen constant ratio K representing the ratio of the second species which has already reacted at the first instant $T_1$ to the value $P_\infty$ representative of the total content of the second species in the rock sample.

The corrected amount $C_v$ is also calculated as a function of the second information $P_{T_2}$ and as a function of the first information $P_{T1}$.

In the particular example, the corrected amount is calculated by the following equation:

$$C_V = \frac{K}{1-K}(P_{T2} - P_{T1}) \quad (5)$$

in which K is the constant ratio, $P_{T_2}$ is the second information and $P_{T_1}$ is the first information.

In the particular example, K is chosen to be between 0.10 and 0.35 and in particular between 0.2 and 0.3, advantageously, approximately equal to 0.24.

In the calculation step 58, the corrected value $C_v$ is subtracted from the information $P_{T_1}$ representative of the cumulative amount of gas compound generated at the first instant, to calculate the corrected relative content $P_1$ of the first species in the rock sample.

In particular, as illustrated in FIG. 5, the relative content $P_1$ is calculated as a function of the first information $P_{T1}$ measured at the first instant T1 minus the corrected amount $C_v$ by the equation:

$$P_1 = P_{T1} - C_v = P_{T1} - \frac{K}{1-K}(P_{T2} - P_{T1}), \quad (6)$$

The relative content $P_2$ of the second species in the rock sample is also calculated based on the corrected amount $C_v$.

The corrected amount $C_v$ is added to the information relative to the cumulative amount of gas compound generated between the first instant and the second instant.

The relative content of the second species is for example calculated by the equation:

$$P_2 = S \cdot \left[(P_{T2} - P_{T1}) + \frac{K}{1-K}(P_{T2} - P_{T1})\right] = \frac{S}{1-K}(P_{T2} - P_{T1}), \quad (7)$$

where S is a stoichiometric corrective factor resulting from the different stoichiometries of reactions 1 and 2.

In particular, since one mole of calcite produces one mole of gas compound and one mole of dolomite produces two moles of gas compound, the corrective factor is equal to:

$$S = \frac{1}{2}\frac{M_{dolomite}}{M_{calcite}} = 0.92, \quad (8)$$

where $M_{dolomite}$ is a molar mass of dolomite and $M_{calcite}$ is the molar mass of calcite.

The method disclosed above is as easy to operate as known methods, especially in a drilling site. The method according to the invention has nevertheless a greater accuracy than known methods. In particular, it avoids large errors in the calculation of the relative contents of the two species, especially when the content of the first species is low.

In a first variant, the method does not comprise a curve fitting step 52. The second information P2 is determined by measuring the information $P_{T2}$ representative of the cumulated amount of gas compound at a second instant T2 which is subsequent to the first instant T1 and which is for example in higher than several minutes after the start of reaction.

In the first variant, the data acquisition step from the sensor 24 at any instant may be omitted. The method may comprise the acquisition of information measured by sensor 24 only at the first instant T1 and only at the second instant T2.

Figure 6:
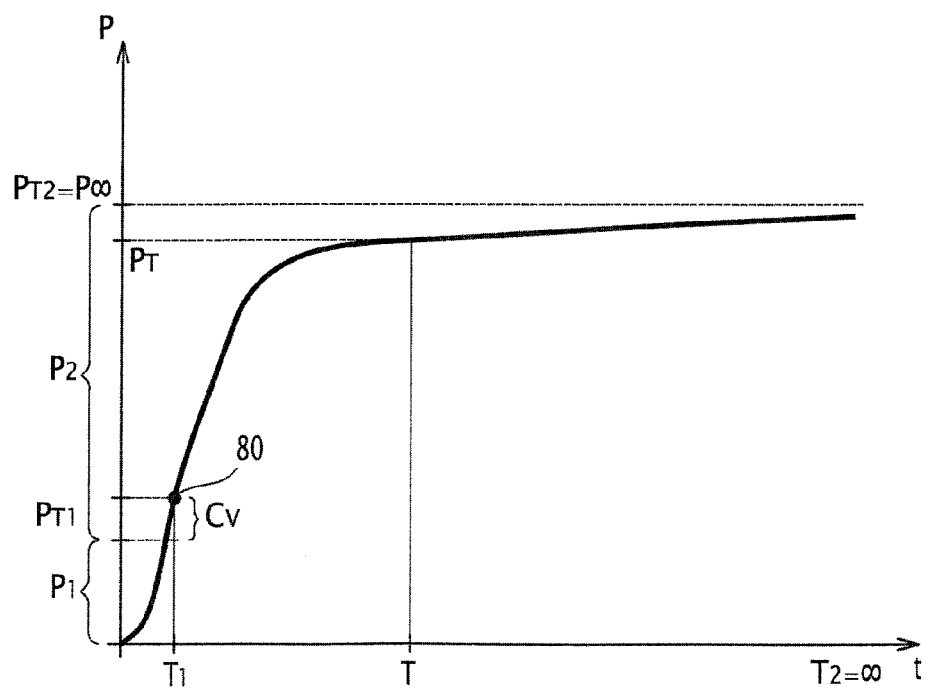
FIG. 6 is a curve similar to FIG. 5 illustrating a second method according to the invention.

A second method according to the invention is illustrated in FIG. 6.

Contrary to the first method shown in FIG. 5, the first instant T1 is not predetermined to be constant for each measured sample.

The method comprises an additional step of determination of the first instant T1.

Advantageously, the method comprises determining an inflexion point 80 on the representative information (in this example pressure) versus time curve. The first instant is then chosen to be at or in the vicinity of the inflexion point 80.

In other respects, the second method is similar to the first method.

Figure 7:
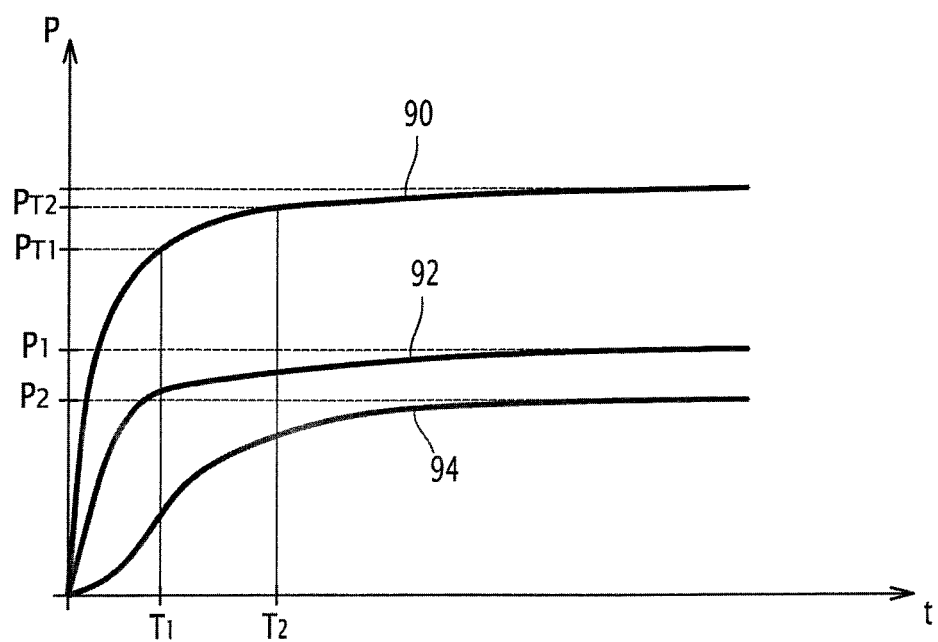
FIG. 7 is a curve similar to FIG. 5 illustrating a third method according to the invention.

A third method according to the invention is depicted in FIG. 7.

In the third method, the representative information versus time curve 90 is recorded by the acquisition module 30 at a sample period lower than e.g. 50 Hz, so that an information relative to the cumulative amount of compound produced at any instant, in particular at a first instant T1 and at a second instant T2 are measured.

Then, the curve 90 is deconvoluted into a first deconvoluted curve 92 and into a second deconvoluted curve 94. The first deconvoluted curve 92 is representative of the first cumulative amount of gas compound resulting from the reaction of the first species with the reactant as a function of time. The second deconvoluted curve 94 is representative of the second cumulative amount of gas compound produced by the reaction of the second species with the reactant as a function of time.

As a consequence, at any instant T, a corrected amount of compound generated by the reaction of the second species with the reactant is evaluated and is used to calculate the relative content of the first species and the relative content of the second species.

In the deconvolution step, the first deconvoluted curve 92 is determined by a first function of the type:

$$P_1(t) = P_1\left(1 - \exp\left[\frac{-t}{\tau_1}\right]\right), \quad (9)$$

in which $P_1$ is a value representative of the total amount of the first species contained in the rock sample and $\tau_1$ is a constant representative of the kinetics of the reaction of the first species.

The second deconvoluted curve 94 is determined by a second function of the type:

$$P_2(t) = P_2\left(1 - \exp\left[\frac{-t}{\tau_2}\right]\right), \quad (10)$$

in which $P_2$ is a value representative of the total amount of the second species in the rock sample and $\tau_2$ is a constant which is a representative of the kinetics of reaction of the second species.

The deconvolution is made using known mathematical optimization methods.

In a variation, the sensor 24 is also able to measure the temperature in the internal volume 20. The cumulative molar amount C can then be calculated based on the measured temperature, e.g. with equation (3).

The invention claimed is:

1. A method for determining the relative content of a first rock species and of a second rock species in a rock sample extracted from a wellbore, the method comprising the following steps:
    adding a reactant to the rock sample, the reactant reacting simultaneously with the first rock species and with the second rock species to produce a compound, the rate of reaction of the reactant with the first rock species being faster than the rate of reaction of the reactant with the second rock species;
    measuring a first information ($P_{T1}$) relative to a first cumulative amount of compound produced at a first instant ($T_1$) and a second information ($P_{T2}$) relative to a second cumulative amount of compound produced at a second instant ($T_2$) subsequent to the first instant ($T_1$);
    calculating the relative content of the first species in the rock sample at least from the first information ($P_{T1}$) determined at the first instant ($T_1$);
    calculating the relative content of the second species in the rock sample at least from the second information ($P_{T2}$) determined at the second instant ($T_2$);
    wherein the method comprises:
    determining a corrected amount (Cv) of compound generated by the reaction of the second species with the reactant at the first instant ($T_1$), and
    calculating the relative content of the first species in the rock sample and the relative content of the second species in the rock sample based on the corrected amount (Cv).

2. The method according to claim 1, wherein the determination step comprises calculating the corrected amount (Cv) of compound based on at least an estimated proportionality constant (K) estimating the relative amount of gas compound generated by the reaction of the second species with the reactant at the first instant to the total amount of compound generated by the reaction of the second species with the reactant.

3. The method according to claim 2, wherein the corrected amount is calculated based on at least one of the first information ($P_{T1}$) representative of the first amount of compound produced at the first instant ($T_1$) and of the second information ($P_{T2}$) relative to the second amount of compound produced at the second instant ($T_2$).

4. The method according to claim 3, wherein the corrected amount (Cv) is given by the equation $$\frac{K}{1-K}(P_{T2} - P_{T1})$$

where n is me estimated proportionality constant, $P_{T1}$ is the first information relative to the first amount of compound produced at the first instant and $P_{T2}$ is the second information relative to the second amount of compound produced at the second instant.

5. The method according to claim 2, wherein the relative content of the first species in the rock sample is calculated by subtracting the corrected amount (Cv) to the first information ($P_{T1}$) representative of the first amount of compound produced at the first instant and in that the relative amount of the second compound is calculated by adding the corrected amount (Cv) to the second information ($P_{T2}$) representative of the second amount of compound produced at the second instant ($T_2$) minus the first information ($_{T1}$) representative of the first amount of compound produced at the first instant ($T_1$).

6. The method according to claim 1, wherein the determination step of the corrected amount (Cv) comprises the following steps:
    obtaining a cumulative curve relating the cumulative amount of generated compound as a function of time based at least on the first information and on the second information;
    deconvoluting the cumulative curve into a first deconvoluted curve representative of the amount of compound produced by the first species as a function of time and a second deconvoluted curve representative of the amount of compound produced by the second species versus time;
    calculating the relative content of the first species and the relative content of the second species based on the first deconvoluted curve and on the second deconvoluted curve.

7. The method according to claim 6, wherein the first deconvoluted curve comprises an exponential function, in particular a function of the type $$P_1\left(1 - e^{\left(\frac{-t}{\tau 1}\right)}\right),$$

in which is the relative content of the first species in the rock sample, t is the time and $\tau_1$ is a constant representative of the kinetics of reaction of the first compound with the reactant and in that the second deconvoluted curve comprises an exponential function, in particular of the type $$P_2\left(1 - e^{\left(\frac{-t}{\tau 2}\right)}\right),$$

in which P2 is the relative content of the second species and $\tau_2$ is a constant representative of the kinetics of reaction of the second species with the reactant.

8. The method according to claim 1, wherein it comprises the steps of:
    measuring a curve of an information representative of the cumulative amount of compound generated as a function of time;

determining an inflexion point on the curve;
determining the first instant ($T_1$) based on the time at which the inflexion point is calculated.

9. The method according to claim 1, wherein it comprises:
measuring a curve of an information representative of the cumulative amount of compound generated as a function of time;
fitting the curve to a pre-determined function;
calculating an information ($P\infty$) representative of total amount of compound generated by the reaction of the reactant with the first species and with the second species based on the fitted function;
calculating the relative content of the second species in the rock sample based on the information representative of the total amount ($P\infty$).

10. The method according claim 1, wherein the first rock species is calcite and the second rock species is dolomite.

11. A device for determining the relative content of a first rock species and of a second rock species in a rock sample extracted from a wellbore, the device comprising:
an enclosure able to receive the rock sample and a reactant, the reactant reacting simultaneously with the first rock species and with the second rock species to produce a compound, the rate of reaction of the reactant with the first rock species being faster that the rate of reaction of the reactant with the second rock species;
a means for measuring a first information ($P_{T1}$) relative to a first cumulative amount of compound produced at a first instant ($T_1$) and for measuring a second information ($P_{T2}$) relative to a second amount of compound produced at a second instant ($T_2$) subsequent to the first instant ($T_1$);
a means for calculating the relative content of the first species in the rock sample at least from the first information determined at the first instant ($T_1$);
a means for calculating the relative content of the second species in the rock sample at least from the second information determined at the second instant;
wherein the device comprises:
a means for determining a corrected amount (Cv) of compound generated by the reaction of the second species with the reactant at the first instant ($T_1$); and
a means for calculating the relative content of the first species in the rock sample and the relative content of the second species in the rock sample based on the corrected amount (Cv).

* * * * *